US00PP37296P3

(12) United States Plant Patent
Bacon et al.

(10) Patent No.: US PP37,296 P3
(45) Date of Patent: Mar. 3, 2026

(54) GRAPEVINE PLANT NAMED 'SUGRA69'

(50) Latin Name: *Vitis vinifera*
Varietal Denomination: SUGRA69

(71) Applicant: Sun World International, LLC, Wasco, CA (US)

(72) Inventors: Terry A. Bacon, Maplewood, NJ (US); Terrence J. Frett, Bakersfield, CA (US)

(73) Assignee: Sun World International, LLC, Wasco, CA (US)

( * ) Notice: Subject to any disclaimer, the term of this patent is extended or adjusted under 35 U.S.C. 154(b) by 0 days.

(21) Appl. No.: 19/041,745

(22) Filed: Jan. 30, 2025

(65) Prior Publication Data

US 2025/0301932 P1 Sep. 25, 2025

(30) Foreign Application Priority Data

Mar. 22, 2024 (PE) ..... 540-2024/DIN

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./205, 206, 207
See application file for complete search history.

(56) References Cited

U.S. PATENT DOCUMENTS

PP20,491 P2 * 11/2009 Striem ..... Plt./207
PP23,837 P3 * 8/2013 Sheehan ..... A01H 5/08
Plt./207

* cited by examiner

*Primary Examiner* — Susan Mccormick Ewoldt
(74) *Attorney, Agent, or Firm* — Knobbe, Martens, Olson & Bear, LLP

(57) ABSTRACT

The new variety of grapevine 'SUGRA69' is characterized by the production of a large-sized, green and obtuse ovate berry with an early season ripening date. The berries of 'SUGRA69' are moderately firm and very juicy.

1 Drawing Sheet

Latin name of the genus and species claimed: *Vitis vinifera.*

Variety denomination: 'SUGRA69'.

CROSS-REFERENCE TO RELATED APPLICATIONS

This application claims the benefit of Peruvian Application No. 540-2024/DIN, filed on Mar. 22, 2024, which is incorporated by reference herein in its entirety.

BACKGROUND AND SUMMARY

This application relates to the discovery and asexual propagation of a new and distinct variety of grapevine, 'SUGRA69', as herein described and illustrated. The new variety was first selected as breeder number 'GR969W' by Terry A. Bacon and Terrence J. Frett in Wasco, Kern County, California in July 2020. The variety was originated by controlled hybridization.

The new variety 'SUGRA69' is characterized by the production of a large-sized, green and obtuse ovate berry with an early season ripening date. The berries of 'SUGRA69' are moderately firm and very juicy.

The seed parent is 'GR548W' (Unpatented) and the pollen parent is 'GR617R' (Unpatented). The parent varieties were first crossed in April 2018. The date of first sowing is March 2019, and the date of first flowering is April 2020.

The new variety 'SUGRA69' was first asexually propagated in December 2020 in Wasco, Kern County, California, by Terry A. Bacon and Terrence J. Frett using hardwood cuttings.

The fruit of the new variety 'SUGRA69' is distinguished from its seed parent 'GR548W' (Unpatented) in that while both have green colored berries with rudimentary seed traces, the new variety 'SUGRA69' has an obtuse ovate berry shape compared to a broad elliptic berry shape for 'GR548W'. Additionally, the new variety 'SUGRA69' has a larger berry weight at 7.6 g with a cluster weight of 625 g compared to a berry weight of 6 g and a cluster weight of 400 g for 'GR548W'.

The new variety 'SUGRA69' is distinguished from its pollen parent 'GR617R' (Unpatented) in that while the berries of the varieties begin ripening at a similar time, the new variety 'SUGRA69' has green berries while 'GR548W' has red berries. Additionally, the new variety 'SUGRA69' has an obtuse ovate berry shape compared to the broad elliptic berry shape for 'GR617R'.

The berries of the new variety 'SUGRA69' being ripening at a similar time as the berries of 'Sheegene-21' (U.S. Plant Pat. No. 23,837), but the berries of the new variety 'SUGRA69' have an obtuse ovate shape compared to the broad elliptic berry shape of 'Sheegene-21'.

The fruit of the new variety 'SUGRA69' has rudimentary seed traces like 'Sugrathirtyfive' (U.S. Plant Pat. No. 20,491), but the berries of the new variety 'SUGRA69' have an obtuse ovate shape compared to the broad elliptic berry shape of 'Sugrathirtyfive'. Additionally, the new variety 'SUGRA69' has an earlier berry ripening of July 18 compared to September 1 for 'Sugrathirtyfive'. Further, the new variety 'SUGRA69' has a smaller berry weight at 7.6 g, compared to 11 g for 'Sugrathirtyfive'.

The new variety 'SUGRA69' has green berries with rudimentary seed traces like 'Autumn King' (U.S. Plant Pat. No. 16,284), but the ripening of the berries of the new variety 'SUGRA69' begins earlier, on July 18, compared to September 3 for 'Autumn King'. Additionally, the new variety 'SUGRA69' has a smaller berry weight at 7.6 g, compared to 12 g for 'Autumn King'.

The new variety 'SUGRA69' has been shown to maintain its distinguishing characteristics through successive asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration taken from a 3-year-old plant shows typical specimens of the foliage and fruit of the present new grape variety 'SUGRA69'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, sixth edition, 2015.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to three-year-old 'SUGRA69' plants grown in the vicinity of Wasco, Kern County, California during 2022, and is believed to apply to plants of the variety grown under similar conditions of soil and climate elsewhere.

VINE

General: (Measurements taken on a three-year-old plant).

- *Vine size.*—Large. Height: Approximately 2.0 m. Width: Approximately 2.5 m.
- *Vigor.*—Medium vigor.
- *Density of foliage.*—Dense.
- *Productivity.*—Very productive.
- *Crop load.*—Approximately 30 kg per vine after thinning.
- *Own root.*—Yes.
- *Training method.*—Typically spur pruned leaving about 40 2-bud spurs.
- *Resistance.*—Neither resistance nor susceptibility to particular diseases or pests has been observed in this variety.

Trunk:

- *Shape.*—Stocky.
- *Diameter.*—Approximately 5 cm (at 30 cm above the soil line).
- *Straps.*—Short.
- *Surface texture.*—Medium shaggy.
- *Inner and outer bark color.*—Inner bark about Medium Greyed-Orange 166C and weathering to about Dark Greyed-Green 197B in the outer bark.

SHOOTS

Young shoot:

- *Form of tip.*—Wide open.
- *Intensity of anthocyanin coloration of tip.*—Absent or very weak.
- *Density of prostrate hairs on tip.*—Medium.
- *Density of erect hairs on tip.*—Absent or very sparse.
- *Color.*—About Medium Green 134B.

Woody shoot (observations made in the middle third of shoot):

- *Attitude before tying.*—Semi-drooping.
- *Growth of axillary shoots.*—Medium, about 20 cm in length.
- *Internode length.*—Short, approximately 70 mm.
- *Width at node.*—Approximately 10 mm.
- *Cross section.*—Circular.
- *Surface texture.*—Striate.
- *Main color.*—About Medium Greyed-Orange 166D.
- *Color of dorsal side of internode.*—About Medium Greyed-Orange 166D.
- *Color of ventral side of internode.*—About Medium Greyed-Orange 166D.
- *Color of dorsal side of node.*—About Medium Greyed-Orange 166D.
- *Color of ventral side of node.*—About Medium Greyed-Orange 166D.
- *Density of erect hairs on nodes.*—Absent.
- *Density of erect hairs on internodes.*—Absent or Very Sparse.
- *Density of prostrate hairs on internodes.*—Absent or Very Sparse.
- *Density of prostrate hairs on nodes.*—Absent or Very Sparse.

Tendrils:

- *Distribution on the shoot at full flowering.*—Discontinuous.
- *Thickness.*—Approximately 2 mm.
- *Color.*—About Light Green 141D.
- *Form.*—Trifurcated.
- *Number of consecutive tendrils.*—Up to 2.
- *Length of tendril.*—Short, approximately 12 cm.

LEAVES

Young leaves:

- *Color of upper surface of first 4 distal unfolded leaves.*—About Medium Green 141C.
- *Average intensity of anthocyanin coloration of six distal leaves prior to flowering.*—Absent or very slight.

*Density of prostrate hairs between veins at lower surface of 4th distal unfolded leaf.*—Absent or very sparse.
*Density of erect hairs between veins at lower surface of 4th distal unfolded leaf.*—Absent or very sparse.
*Density of prostrate hairs on veins at lower surface of 4th distal unfolded leaf.*—Absent or very sparse.
*Density of erect hairs on veins at lower surface of 4th distal unfolded leaf.*—Absent or very sparse.

Mature leaves (observations made on leaves in the middle third of shoot):
*Size.*—Large.
*Average length.*—Approximately 11 cm.
*Average width.*—Approximately 13 cm.
*Shape of blade.*—Pentagonal.
*Number of lobes.*—Approximately 5.
*Mature leaf profile.*—Undulate.
*Blistering surface of blade upper surface.*—Absent or very weak.
*Leaf blade tip.*—In the plane of the leaf.
*Undulation of margin.*—Slightly undulating.
*Thickness.*—Average-typical of *Vitis vinifera* species.
*Overall shape of teeth.*—Mixture of both sides straight and both sides convex.
*Length of teeth.*—Medium, ranging from about 5 mm to 10 mm, usually 10.
*Ratio length/width of teeth.*—Very small, nearly 1:1.
*General shape of petiole sinus lobes.*—Half open.
*Tooth at petiole sinus.*—Absent.
*Petiole sinus limited by veins.*—Absent.
*Shape of upper lateral sinus lobes.*—Slightly overlapping.
*Depth of upper lateral sinuses.*—Deep, approximately 4 cm to 5 cm.
*Density of prostrate hairs between veins on lower surface of blade.*—Absent to very sparse.
*Density of erect hairs between veins on lower surface of blade.*—Absent to very sparse.
*Density of prostrate hairs on main veins on lower surface of blade.*—Absent to very sparse.
*Density of erect hairs on main veins on lower surface of blade.*—Absent to very sparse.
*Density of prostrate hairs on main veins on upper surface of blade.*—Absent to very sparse.
*Autumn coloration of leaves.*—Usually about Light Green 138B becoming about Medium Grey-Brown 199C.

Upper leaf surface:
*Color.*—About Dark Green 133B.
*Surface texture.*—Smooth.
*Surface appearance.*—Dull.
*Anthocyanin coloration of main veins.*—Absent or very low.

Lower leaf surface:
*Color.*—About Light Green 135D.
*Surface texture.*—Smooth.
*Surface appearance.*—Dull.
*Anthocyanin coloration of main veins.*—Absent or very low.

Petiole:
*Length of petiole.*—Approximately 7 cm.
*Diameter.*—Approximately 3 mm.
*Length of petiole compared to middle vein.*—Slightly shorter, 7 cm for the petiole compared to 11 cm for middle vein.
*Density of prostrate hairs on petiole.*—Absent.
*Density of erect hairs on petiole.*—Absent.
*Color.*—About Light Green 142B.

Buds:
*Shape.*—Conical.
*Size.*—Medium, approximately 3 mm wide×4 mm long.
*Position.*—Slightly held out.
*Bud fruitfulness.*—Basal, mostly fruitful.
*Time of bud burst.*—Early, approximately March 15th for the southern San Joaquin Valley region of California.

FLOWERS

General:
*Flower type.*—Fully developed stamen and fully developed gynoecium.
*Position of first flowering node.*—Usually 5th node of current season growth.
*Number of inflorescences per shoot.*—Usually 1 per shoot.
*Time of full bloom.*—Approximately May 9th in the southern San Joaquin Valley region of California.
*Size.*—Approximately 20 mm to 30 mm.
*Number of petals.*—About 5.
*Color.*—About Dark Green NN137A and Dark Green NN137B.
*Type of inflorescence.*—Paniculate with perfect flowers.

FRUIT

General:
*Ripening period.*—Early season, beginning about July 18th in the southern San Joaquin Valley region of California.
*Use.*—Fresh market.
*Storage quality.*—Good.

Cluster:
*Form.*—Long conical.
*Cluster size (peduncle excluded).*—Medium.
*Cluster length (peduncle excluded).*—Approximately 29 cm.
*Cluster width.*—Approximately 22 cm.
*Cluster weight.*—Approximately 625 g.
*Cluster density.*—Loose, some visible pedicels.
*Number of berries.*—Approximately 100 berries after tipping.

Peduncle:
*Length.*—Long, approximately 3 cm.
*Diameter.*—Approximately 10 mm.
*Lignification of peduncle.*—Weak.
*Color.*—About Medium Green 143B.

Berry:
*Size.*—Large, approximately 7.6 g.
*Dimensions.*—Width: Approximately 26 mm. Length: Approximately 30 mm.
*Uniformity of size.*—Somewhat uniform.
*Shape.*—Obtuse ovate.
*Cross section.*—Circular.
*Skin color (without bloom).*—About Strong Yellow Green 145A, Strong Yellow Green N144D, and Light Yellow Green 145B.
*Flesh color.*—About Light Yellow Green 145C, Light Yellow Green 145D, and Pale Yellow Green 149D.
*Anthocyanin color of flesh.*—Absent or very weak.

*Bloom* (*cuticular wax*).—Medium, typical of most commercial *Vitis vinifera*.
*Pedicel length*.—Approximately 13 mm.
*Pedicel thickness*.—Medium, approximately 1.8 mm.
*Berry separation from pedicel*.—Moderately easy.
*Seed traces*.—Rudimentary.
*Berry firmness*.—Moderately firm.
*Flesh Juiciness*.—Very juicy.
*Flesh texture*.—Firm and meaty.
*Particular flavor*.—Tropical muscat.
*Refractometer test*.—About 21 Brix.
*Juice ph*.—About 3.56.
*Titratable acidity*.—About 0.35%.
*Brix:acid ratio*.—Approximately 60.

Skin:
*Skin thickness*.—Medium, about 175 μm.
*Skin texture*.—Smooth.
*Skin reticulation*.—Absent.
*Skin tenacity*.—Tenacious to flesh.
*Skin tendency to crack*.—Rare.
*Skin sensitivity to sunburn*.—None.

What is claimed is:

1. A new and distinct variety of grapevine plant named 'SUGRA69', as illustrated and described herein.

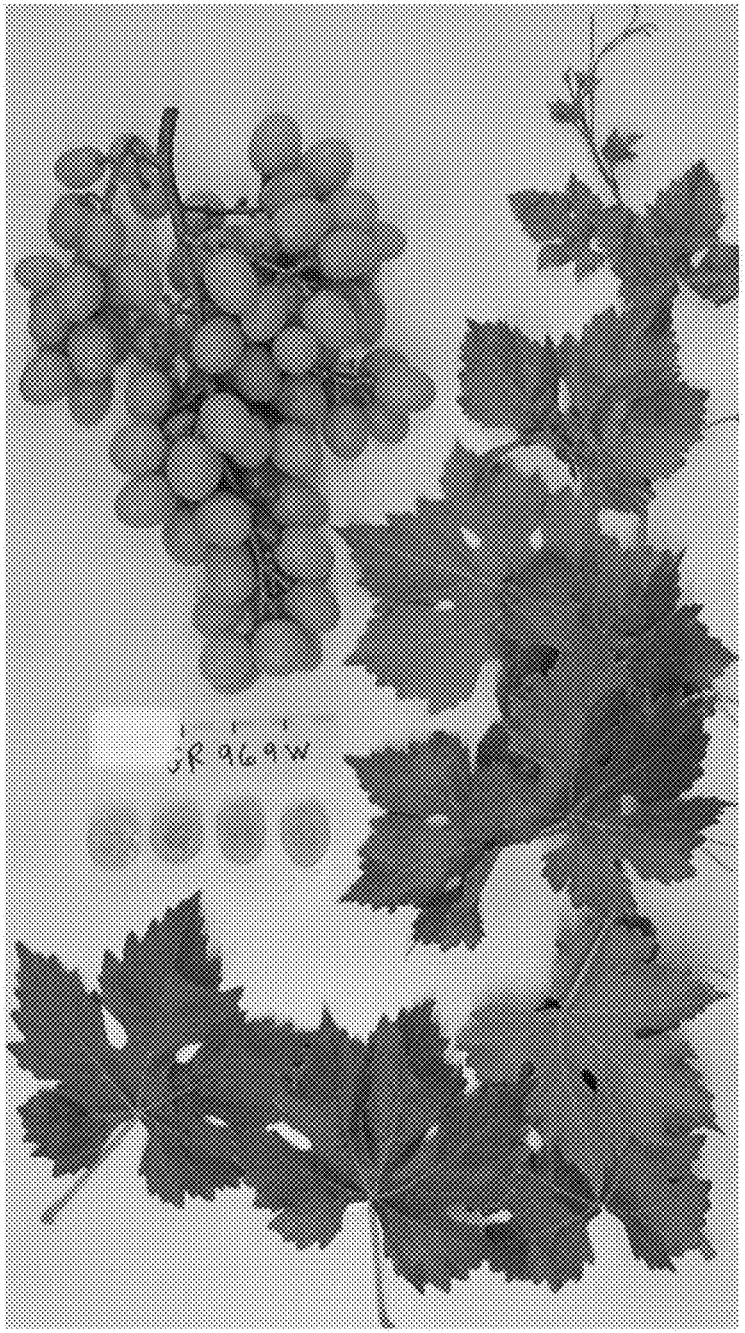

* * * * *